United States Patent [19]
Clark

[11] Patent Number: 6,139,500
[45] Date of Patent: Oct. 31, 2000

[54] METHODS AND APPARATUS FOR 3D CARDIAC ULTRASOUND IMAGING

[75] Inventor: David W Clark, Windham, N.H.

[73] Assignee: Agilent Technologies Inc., Palo Alto, Calif.

[21] Appl. No.: 09/256,955

[22] Filed: Feb. 24, 1999

[51] Int. Cl.$^7$ .................................................. A61B 8/00
[52] U.S. Cl. .......................................... 600/443; 128/916
[58] Field of Search .................................. 600/437, 443, 600/441, 444, 447; 128/916

[56] References Cited

U.S. PATENT DOCUMENTS

| | | | |
|---|---|---|---|
| Re. 30,397 | 9/1980 | King ........................................ | 128/916 |
| 5,159,931 | 11/1992 | Pini .................................... | 128/660.07 |
| 5,315,512 | 5/1994 | Roth ........................................ | 600/443 |
| 5,337,752 | 8/1994 | Reeves .................................... | 128/700 |
| 5,435,310 | 7/1995 | Sheehan et al. ..................... | 128/653.1 |
| 5,666,955 | 9/1997 | Kondo et al. ........................... | 600/440 |
| 5,766,129 | 6/1998 | Mochizuki ............................... | 600/443 |
| 5,976,088 | 11/1999 | Urbano et al. ......................... | 600/443 |
| 5,993,390 | 11/1999 | Savord et al. ...................... | 128/916 X |
| 6,056,691 | 5/2000 | Urbano et al. ......................... | 600/443 |

OTHER PUBLICATIONS

Takahiro Ota et al, Novel Determination of Left Ventricular Vol. by Tracing Arbitrary Planes Using Real–Time, 3D Echocardiography: In Vitro and In Vivo Validation, 70th Scientific Session American Heart Assn. Meeting Nov. 11, 1997, p. 1832.

Takahiro Ota et al., "Accuracy of Left Ventricular Stroke Volume Management Using Real–Time, Three Dimensional Echocardiography & Electromagnetic Flow Probe in Vivo", 70th Scientific Session American Heart Assn. Meeting, Nov. 11, 1997, p. 1831.

Craig E. Fleishman et al, "Evaluation of Atrioventricular Valve Abnormalities Using Real–Time Three–Dimensional Echocardiography", 70th Scientific Session American Heart Assn. Meeting, Nov. 11, 1997, p. 1045.

Ming Shu et al, "Tricuspid Velocity Profiles Reflect Right Ventricular Diastolic Wall Motion Abnormalities: Real–Time 3D Echocardiography and Computational Fluid Dynamics", 70th Scientific Session American Heart Assn. Meeting, Nov. 11, 1997, p. 2990.

Takahiro Shiota et al, "Application of a New Real–Time Three–Dimensional Method for Evaluating Right Ventricular Stroke Volume", 70th Scientific Session American Heart Assn. Meeting, Nov. 11, 1997, p. 1830.

*Primary Examiner*—Francis J. Jaworski

[57] ABSTRACT

Methods and apparatus are provided for medical ultrasound imaging. An ultrasound beam is scanned in a fast scan direction and is scanned in a slow scan direction concurrently with scanning in the fast scan direction. During scanning of the ultrasound beam, ultrasound data samples, representative of two-dimensional slices of a volume of interest in a patient, are acquired at different points in the slow scan direction and at different times in the patient's cardiac cycle. Scanning in the slow scan direction is controlled relative to the patient's cardiac cycle so that the acquired data samples have a desired spatial distribution over the volume of interest and a desired temporal distribution over the patient's cardiac cycle. The acquired data samples are converted to three-dimensional image data sets which represent the volume of interest at different times in the patient's cardiac cycle. Scanning in the slow scan direction may be controlled by starting scanning at uniformly-spaced time intervals relative to the patient's cardiac cycle.

24 Claims, 7 Drawing Sheets

METHODS AND APPARATUS FOR 3D CARDIAC ULTRASOUND IMAGING

FIELD OF THE INVENTION

This invention relates to medical ultrasound imaging and, more particularly, to methods and apparatus for three-dimensional cardiac ultrasound imaging.

BACKGROUND OF THE INVENTION

Medical ultrasound imaging systems typically use a one-dimensional phased array to form an image of a two-dimensional slice through a patient's body. This approach has limitations. First, the two-dimensional slice is perpendicular to the face of the transducer, thereby limiting the choice of views. Second, anatomy such as the left ventricle is inherently three-dimensional. To obtain an accurate volume measurement of the left ventricle, three-dimensional data must be acquired. A goal in three-dimensional cardiac imaging is to obtain a measure of the volume of the left ventricle in both end systole and end diastole, so that ejection fraction and cardiac output can be estimated.

In current solutions, such as Hewlett-Packard's Sonos 5500, a two-dimensional slice of data is acquired per cardiac phase during each heartbeat. For a volume of 120 two-dimensional slices, 120 heartbeats are required to acquire the volume data. Cardiac, respiratory, patient whole body and sonographer motion occur during this long acquisition. Cardiac motion may be frozen by using an ECG trigger. Respiratory motion may be reduced through the use of either multiple breathholds or respiratory gating. However, since the heart does not return to the same position from breath to breath or from breathhold to breathhold, discontinuities are introduced into the acquired data. Patient and sonographer motion also cause discontinuities and overall geometric distortion.

A system capable of acquiring real-time, three-dimensional data by electronically steering in two dimensions is described by T. Ota et al. in "Accuracy of Left Ventricular Stroke Volume Measurement Using Real-Time, Three-Dimensional Echocardiography Flow Probe in Vivo", 70th Scientific Session American Heart Association Meeting, Nov. 11, 1997. This system uses 512 active transducer elements. Signals from the transducer elements are passed through a cable having 512 coaxial conductors into a system with appropriate electronics. The image quality of the system is limited due to the small number of transducer elements used.

Apparatus for obtaining a three-dimensional reconstruction of anatomic structures through the acquisition of two-dimensional ultrasound images is disclosed in U.S. Pat. No. 5,159,931 issued Nov. 3, 1992 to Pini. One or more two-dimensional images are acquired during alternate heartbeats of a patient. When more than one two-dimensional image is acquired during a single heartbeat, the images represent a constant two-dimensional slice of the patient's heart at different phases of the cardiac cycle. During alternate heartbeats when images are not being acquired, the transducer is rotated to a new position. Rotation of the transducer may be performed mechanically using a stepping motor or electronically using a matrix or multiple arrays of transducer elements. Acquisition of a three-dimensional image requires 120 heartbeats.

All of the known prior art three-dimensional cardiac imaging techniques have had low resolution and/or long acquisition times. In the case of long acquisition times, the images typically exhibit discontinuities due to cardiac, respiratory, patient and/or sonographer movement. Accordingly, there is a need for improved methods and apparatus for three-dimensional cardiac ultrasound imaging.

SUMMARY OF THE INVENTION

According to a first aspect of the invention, a method is provided for medical ultrasound imaging of a patient having a cardiac cycle. An ultrasound beam is scanned in a fast scan direction and is scanned in a slow scan direction concurrently with scanning in the fast scan direction. During scanning of the ultrasound beam, ultrasound data samples, representative of two-dimensional slices of a volume of interest in the patient, are acquired at different points in the slow scan direction and at different times in the patient's cardiac cycle. Scanning the slow scan direction is controlled relative to the patient's cardiac cycle, so that the acquired data samples have a desired spatial distribution over the volume of interest and a desired temporal distribution over the patient's cardiac cycle. The acquired data samples are converted to three-dimensional image data sets which represent the volume of interest at different times in the patient's cardiac cycle.

Scanning in the slow scan direction may be controlled by starting scanning in the slow scan direction at uniformly spaced time intervals relative to the patient's cardiac cycle. More particularly, scanning in the slow scan direction may be controlled by defining a plurality of available departure times relative to the patient's cardiac cycle, selecting an unused departure time from the available departure times, starting scanning in the slow scan direction at the selected departure time, and marking the selected departure time as used. Preferably, the spatial and temporal distributions of the acquired data samples are selected such that spatial and temporal variations in an object being imaged may be reconstructed. Preferably, the acquired data samples have a substantially uniform spatial distribution over the volume of interest and have a substantially uniform temporal distribution over the patient's cardiac cycle.

The scanning of the ultrasound beam in the slow scan direction may be unidirectional or bidirectional and may be continuous or stepped. The ultrasound beam may be scanned in the slow scan direction at a speed that is based on a scanning speed in the fast scan direction and the desired sample spacing in the slow scan direction.

In one embodiment, the ultrasound beam is mechanically scanned in the slow scan direction. The mechanical scanning can be translation, rotation, or reciprocation, or may be a combination of some or all of these movements. In another embodiment, the ultrasound beam is electronically scanned in the slow scan direction.

According to another aspect of the invention, apparatus is provided for medical ultrasound imaging of a patient having a cardiac cycle. The apparatus comprises an ultrasound transducer including an array of transducer elements, a transmit beamformer, a scanning device, a receive beamformer, an ECG device, a controller and a scan converter. The transmit beamformer energizes the transducer for transmitting an ultrasound beam into a volume of interest in the patient's body and for scanning the ultrasound beam in a fast scan direction. The scanning device scans the ultrasound beam in a slow scan direction concurrently with scanning in the fast scan direction. The receive beamformer processes received signals, generated by the ultrasound transducer in response to ultrasound echoes received from the volume of interest, to form at least one receive beam for each of the transmitted ultrasound beams. The receive beamformer acquires ultrasound data samples, representative of two-dimensional slices of the volume of interest, at different points in the slow scan direction and at different times in the patient's cardiac cycle. The ECG device is coupled to the patient for generating an ECG signal representative of the patient's cardiac cycle. The controller controls the scanning device in response to the ECG signal so that the acquired data samples have a desired spatial distribution over the volume of interest and a desired temporal distribution over the patient's cardiac cycle. The scan converter converts the acquired data samples to three-dimensional image data sets which represent the volume of interest at different times in the patient's cardiac cycle.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
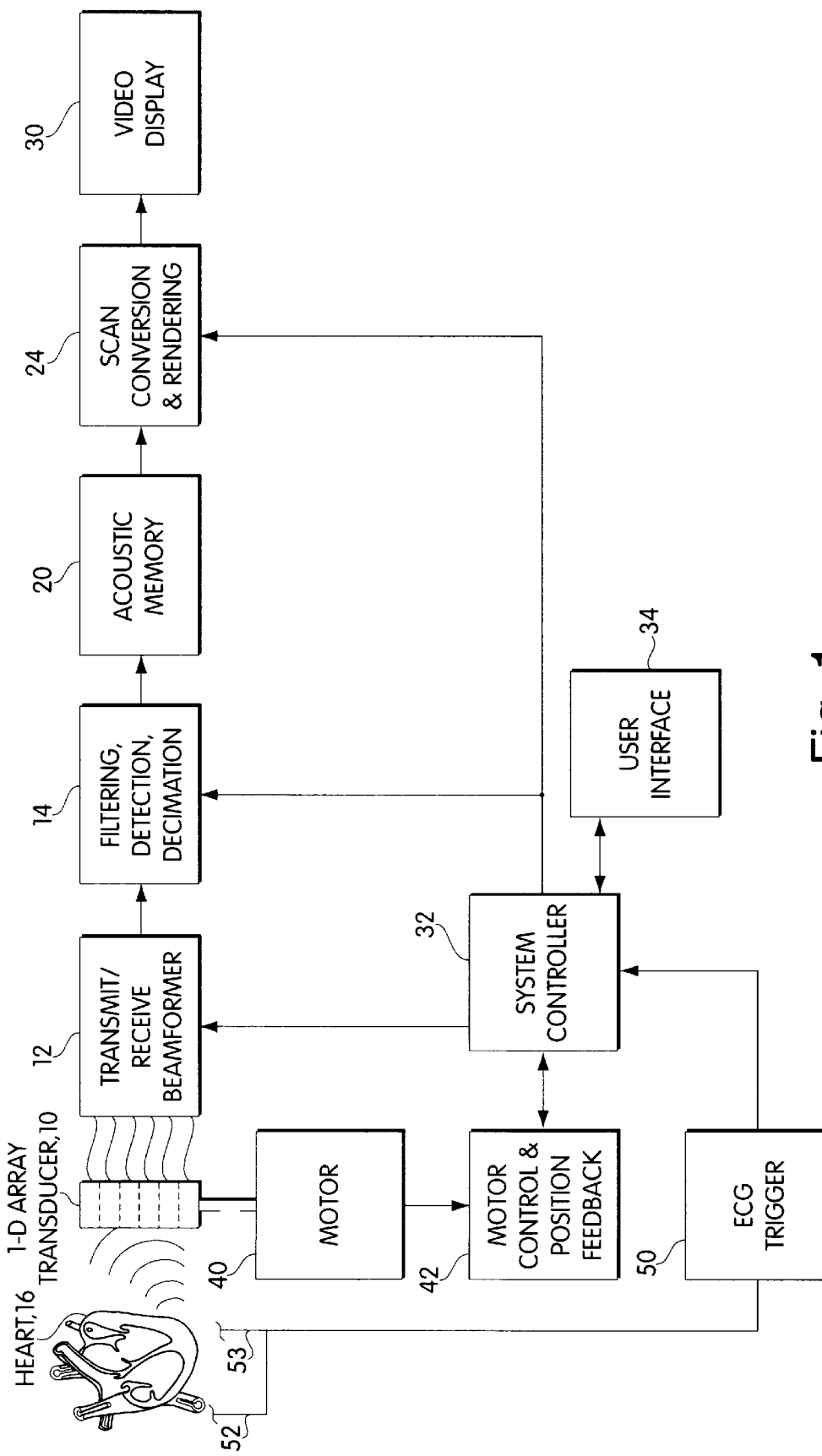
FIG. 1 is a block diagram of an example of an ultrasound imaging system suitable for implementing the present invention.
Figure 2A:
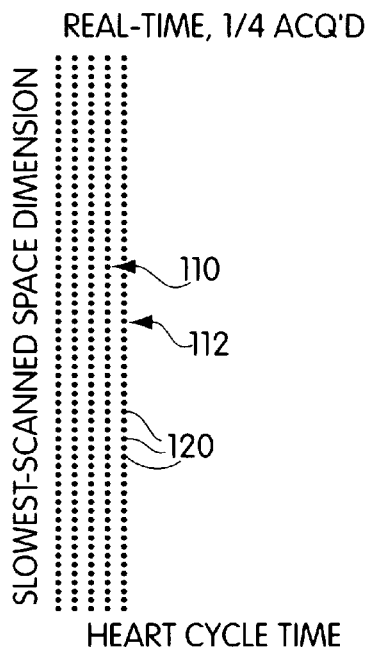
FIGS. 2A, 2B, 2C and 2D are graphs of beam position in a slow scan direction as a function of heart cycle time according to a real time image data acquisition technique.
Figure 2B:
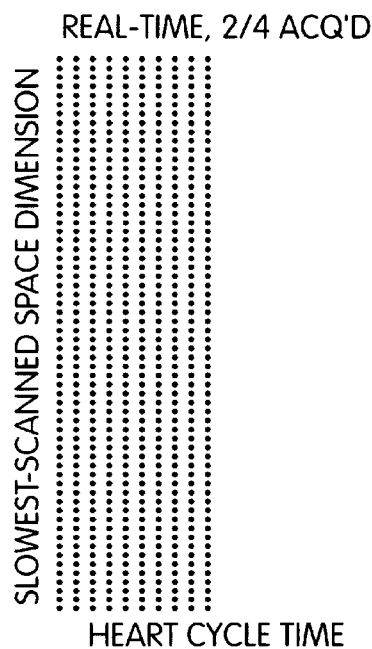
Figure 2C:
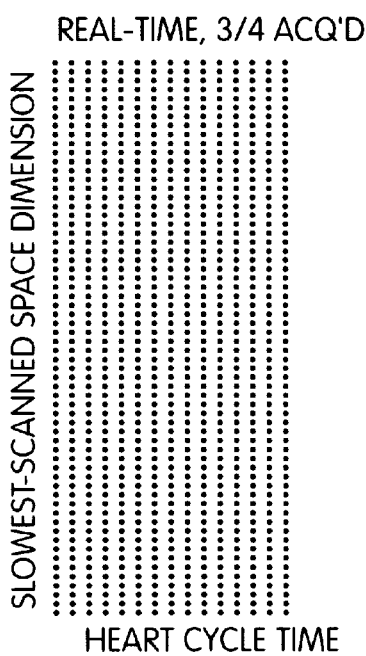
Figure 2D:
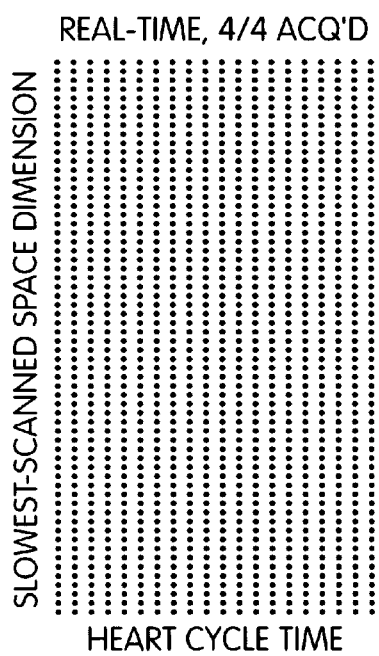
Figure 3A:
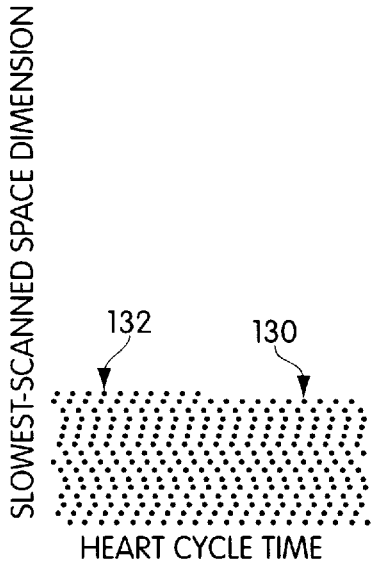
FIGS. 3A, 3B, 3C and 3D are graphs of beam position in a slow scan direction as a function of heart cycle time according to a non-real time image data acquisition technique.
Figure 3B:
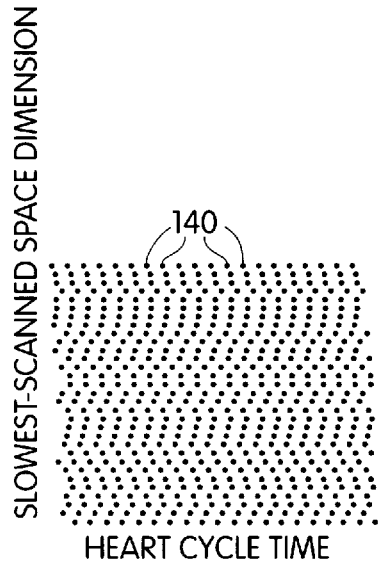
Figure 3C:
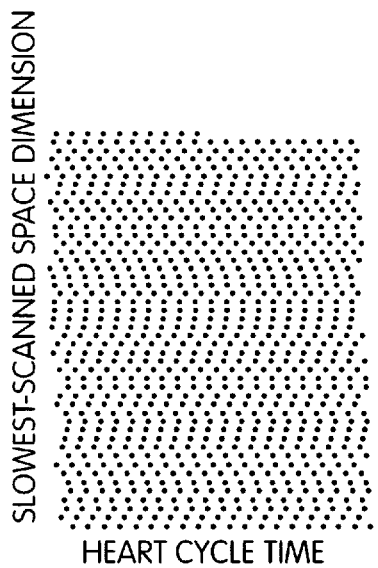
Figure 3D:

A simplified block diagram of an example of an ultrasound imaging system suitable for implementing the present invention is shown in FIG. 1. A transducer array 10 is coupled to a transmit/receive beamformer 12. Transducer array 10 may be a one-dimensional array of transducer elements for performing phased array ultrasound scanning. The transducer array 10 transmits pulses of ultrasound energy into a volume of interest in a patient's body and receives reflected ultrasound energy, or echoes, from various structures and organs within the patient's body. In FIG. 1, the volume of interest is represented by a patient's heart 16. The transmit/receive beamformer 12 includes a transmit beamformer and a receive beamformer, which may be coupled to the transducer elements of transducer array 10 through a transmit/receive switch. By appropriately delaying the pulses applied to each transducer element by the transmit beamformer, a focused ultrasound beam is transmitted along a desired transmit scan line.

In another embodiment, one group of transducer elements in transducer array 10 is dedicated to transmitting ultrasound energy and another group of transducer elements is dedicated to receiving ultrasound energy. In this embodiment, the transmit/receive switch is not required. The transmit beamformer is coupled directly to the dedicated transmit elements of transducer array 10, and the receive beamformer is coupled directly to the dedicated receive elements.

The transducer array 10 is coupled, either directly or through the transmit/receive switch, to the receive beamformer. Reflected ultrasound energy from a given point within the patient's body is received by the transducer elements at different times. The transducer elements convert the received ultrasound energy to received electrical signals, which are amplified and are supplied to the receive beamformer. The signals from each transducer element are individually delayed and then are summed by the receive beamformer to provide a beamformer signal that represents the reflected ultrasound energy level along a given receive scan line. As known in the art, the delays applied to the received signals may be varied during reception of ultrasound energy to effect dynamic focusing. The process is repeated for multiple scan lines to provide signals for generating an image of a region of interest in the patient's body. The receive beamformer, for example, may be a digital beamformer of the type used in the HP Sonos 5500 ultrasound imaging system, manufactured and sold by Hewlett-Packard Company. The digital beamformer produces digital samples of the volume of interest.

The beamformer signals are processed by a filtering, detection and decimation unit 14, and the processed signals are stored in an acoustic memory 20. As described below, acoustic memory 20 stores data samples representative of the volume of interest at different times during a cardiac cycle. The data samples are read from acoustic memory 20 by a scan conversion and rendering unit 24, which converts the stored data samples to a form suitable for generation of an ultrasound image on a video display unit 30.

A system controller 32 provides overall control of the system. The system controller 32 performs timing and control functions and typically includes a microprocessor and a memory. A user interface 34 coupled to system controller 32 permits a user to control operating modes and parameters of the imaging system.

In the embodiment of FIG. 1, transducer array 10 is coupled to a motor 40, which produces mechanical movement of transducer array 10. As described below, the movement may be rotational, translational or reciprocating movement, or may be a combination of some or all of these movements. A motor controller 42 receives control signals from system controller 32 and controls the operation of motor 40. Motor controller 42 includes a position sensor for sensing the position of motor 40 and providing a position feedback signal to system controller 32.

In the embodiment of FIG. 1, the transmit beamformer in transmit/receive beamformer 12 controls electronic scanning of a transmitted ultrasound beam in a two-dimensional plane. The electronic scanning direction is known as a fast scan direction. Motor 40 moves the transducer array 10 to produce scanning of the ultrasound beam in a slow scan direction so that the transmitted ultrasound beam covers the three-dimensional volume of interest. The fast scan direction of electronic scanning may be the azimuth direction, and the slow scan direction of mechanical scanning may be the elevation direction.

In other embodiments, transducer array 10, motor 40 and motor controller 42 are replaced by a two-dimensional transducer array. The transmit/receive beamformer 12 is modified to permit scanning in both azimuth and elevation, thereby providing electronic scanning in three dimensions.

An ECG device 50 includes ECG electrodes 52, 53, etc. attached to the patient. The ECG device 50 supplies an ECG trigger signal to system controller 32 for synchronizing image data acquisition to the patient's cardiac cycle, as described in detail below.

Three-dimensional cardiac image data acquisition can be viewed as a four-dimensional sampling problem, where the fourth dimension is normalized time for the patient's cardiac cycle. The cardiac cycle may be divided into cardiac phases, or intervals, for imaging. Typically one or more images is obtained during each cardiac interval to provide a moving picture of cardiac function. The selection of cardiac interval is typically based on the maximum time in which the heart does not move significantly. A typical cardiac cycle may be on the order of about 800 milliseconds and may be divided into about 10–30 cardiac phases, or intervals, for ultrasound imaging. Thus, about 10–30 images are acquired during the patient's cardiac cycle. More or fewer cardiac intervals phases may be utilized within the scope of the invention.

By obtaining three-dimensional images representing the heart at different times during the patient's cardiac cycle, a variety of information can be obtained. The three-dimensional images of the heart at successive cardiac intervals can be displayed as a function of time to represent heart movement. The moving image can be used to identify end systole and end diastole and to perform other diagnostics. Images of a selected cardiac phase can be rotated to a desired orientation for improved analysis. Image analysis techniques can be utilized to quantify maximum and minimum volumes of the left ventricle. From this information, ejection volume and ejection fraction can be calculated.

Cardiac image data acquisition thus involves acquisition of data samples that cover the three-dimensional volume of interest at a desired number of time intervals during the cardiac cycle. All cardiac cycles are considered substantially equivalent over the elapsed time of the image data acquisition. Minor cycle time variations can be compensated by scaling the time dimension in the scan conversion processing. Data for severe cardiac cycle aberrations should be discarded, and either reacquired or interpolated over. The four dimensions must be adequately sampled to satisfy the Nyquist criterion, meaning roughly that the samples must be close enough together to follow any significant spatial and temporal variation in the heart or other object being imaged. The samples are not required to be uniformly spaced in either rectangular or polar coordinates (although that is desirable), as long as the sample density is adequate to meet the Nyquist criterion and the locations of the samples are known in all four dimensions. The scan conversion processing that is performed after the data is acquired interpolates and resamples the data onto a more convenient uniform rectangular grid.

Ultrasound scanning in two space dimensions is typically performed electronically, using either beam steering or subaperture stepping to acquire data representative of a two-dimensional slice of the volume of interest. Two-way parallelism in this plane improves frame rate without significant image quality degradation. Two-dimensional frame rates with two-way parallelism are on the order of 100 Hz. Electronic scanning in two space dimensions is referred to herein as scanning in a fast scan direction.

Electronic scanning in the third space dimension requires a two-dimensional transducer array and associated electronics. While this approach is desirable, it is relatively complex and expensive at the current state of the art. Various mechanical scanning movements for the third space dimension include rotation, translation, reciprocation and combinations thereof. When the third space dimension is included, the frame rate drops to 1 to 2 Hz, assuming that it is limited by acoustics and not mechanics. This frame rate may be adequate for radiology or obstetric imaging, but it is too slow for real time cardiac imaging. The field of view may be reduced to increase frame rate, but then the entire heart is not visible in the image.

The analysis of sampling patterns in four dimensions may be simplified by noting that the time to acquire data in the fast scan direction, i.e. electronic scanning of a two-dimensional slice, is nearly instantaneous in comparison with the cardiac cycle time. The most significant sampling issues then involve only the slow scan direction, i.e. the mechanical scan direction, and the time dimension. The problem can therefore be analyzed with two-dimensional time/space diagrams.

Real time cardiac data acquisition is shown in the diagrams of FIGS. 2A–2D. Non-real time cardiac data acquisition is shown in the diagrams of FIGS. 3A–3D. The vertical axis in the diagrams is beam position in the slow scan direction (polar or rectangular coordinates). The horizontal axis is heart (cardiac) cycle time and represents one cardiac cycle. A single scan in the fast scan direction is represented by a dot in the diagrams, and the progression of successive two-dimensional acquisitions traces a path in the diagrams. For simplicity, the diagrams show these paths as straight lines, corresponding to a constant speed of traversing the slow scan direction. Where data acquisition requires more than one cardiac cycle, the paths are superimposed on a single cardiac cycle for purposes of illustration. These diagrams are referred to herein as "time/space" diagrams.

Real time data acquisition implies a set of nearly vertical scan paths 110, 112, etc. as shown in FIGS. 2A–2D. Each scan path 110, 112, etc. is made up of multiple scans in the fast scan direction, each represented by a dot 120 in FIGS. 2A–2D. The entire three-dimensional volume of interest is sampled multiple times, typically 10 to 30 times, in the elapsed time of a single cardiac cycle. FIGS. 2A–2D illustrate real time data acquisition after one-quarter, one-half, three-fourths and a full cardiac cycle, respectively. As indicated above, real time data acquisition involves significant complication, cost and/or degradation of image quality.

Non-real time data acquisition implies horizontal scan paths 130, 132, etc., as shown in FIGS. 3A–3D, corresponding to an entire cardiac cycle acquisition with little or no movement in the slow scan direction. Each scan path 130, 132 etc, is made up of multiple scans, etc. in the fast scan direction, each represented by a dot 140 in FIGS. 3A–3D. It will be understood that FIGS. 3A–3D each represent data acquisition after multiple cardiac cycles. The horizontal scan paths 130, 132, etc. have different displacements in the vertical slow scan direction in different cardiac cycles. Assuming that an ECG trigger is used for timing synchronization and that data is retained only for cardiac cycles which are sufficiently similar, the horizontal scan paths 130, 132, etc. are aliased into a single equivalent-time cardiac cycle. The end points of the horizontal scan paths are slightly different because the actual cardiac cycles are not perfectly identical, an effect which is often ignored in three-dimensional reconstruction. Also, if the two-dimensional fast scan acquisitions are free-running rather than ECG triggered, then the samples do not line up in time. This effect is also often ignored in the reconstruction.

Non-real time data acquisition is relatively easy and inexpensive, but is inefficient. Even though the imaging system is capable of two-dimensional frame rates of 50 Hz to 100 Hz, the number of two-dimensional acquisitions in a cardiac cycle is limited to 20 to 30 because that provides adequate time resolution. Additional two-dimensional acquisitions during a cardiac cycle would require more memory and computation than is necessary to obtain good quality images. Furthermore, with mechanical scanning, at least one cardiac cycle is wasted for every cardiac cycle that is acquired because of the time required to step the transducer to the next position. The data acquisition must also be gated to only proceed during the exhaled phase of respiration, both for image alignment and for minimum attenuation through the lungs. These inefficiencies result in acquisition times of several minutes.

In accordance with a feature of the invention, excess system capacity in the time dimension is applied to the slow scan direction by rapidly acquiring two-dimensional fast scan frames, while scanning in the slow scan direction. A challenge of this approach to cardiac data acquisition is to ensure that all parts of the volume of interest are sampled at all phases of the cardiac cycle, without wasting a significant amount of time.

In contrast to the almost vertical scan paths of real time data acquisition (FIGS. 2A–2D) and the horizontal scan paths of non-real time acquisition (FIGS. 3A–3D), the data acquisition technique of the present invention utilizes scan paths that are slanted at an intermediate angle between vertical and horizontal in the time/space diagrams. For example, the time to sample the three-dimensional volume of interest once may be within a factor of three of the cardiac cycle time. The slanted scan paths can be either unidirectional, as with electronic scanning or with continuous mechanical rotation, or may be slanted both up and down, as with reciprocating mechanical scanning. Reciprocating motion is shown in FIGS. 4 and 5A–5H. Faster scanning corresponds to a steeper slope of the slanted scan paths in the time/space diagrams. The scan paths are aliased into an equivalent-time cardiac cycle using an ECG trigger.

Scanning in the slow scan direction can be mechanical or electronic, can be unidirectional or bidirectional, and can be translation, rotation, reciprocation, or combinations of some or all of these movements. The two-dimensional frames may be acquired without any triggering (free-running), may be triggered at the start of each scan in the slow scan direction and then may be free-running through a slow scan, or may be triggered at specific spatial locations based on a position feedback signal from the transducer. The slow scanning and/or the transmit power may be halted except when data acquisition is requested. This is particularly advantageous for a mechanically-scanned transducer, since it limits wear, heat and noise.

Figure 4:
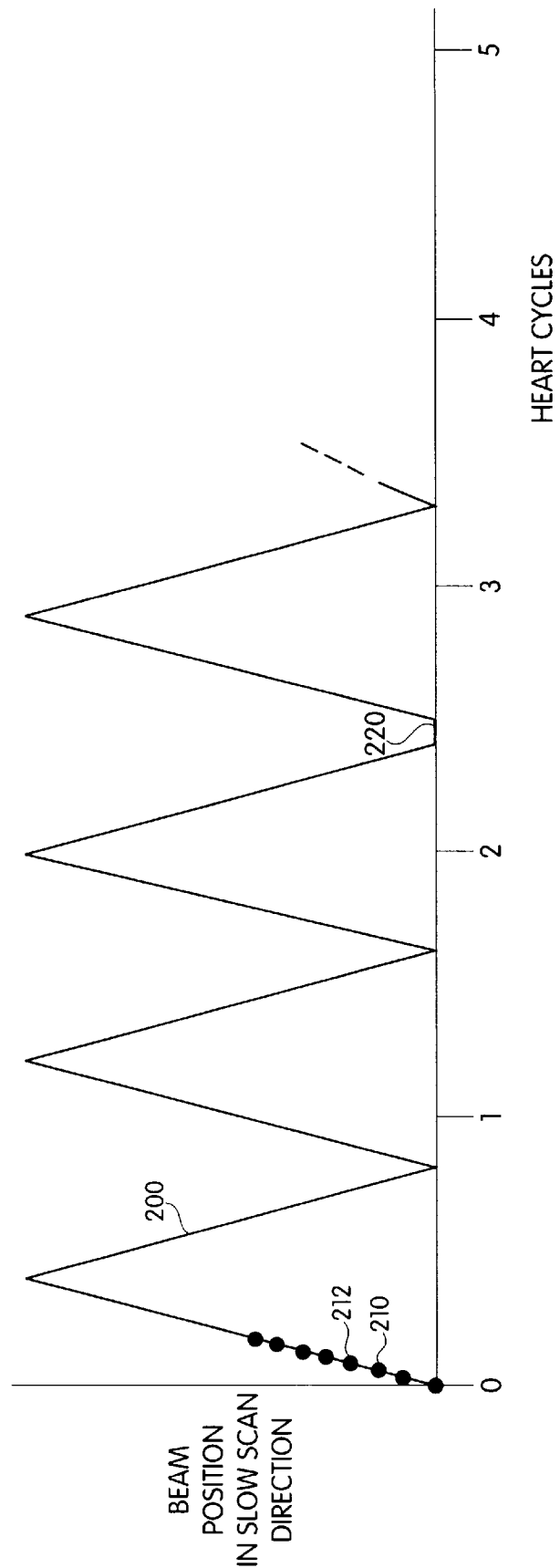
FIG. 4 is a graph of beam position in a slow scan direction as a function of heart cycle time, showing an embodiment of image data acquisition in accordance with the present invention.
Figure 5A:
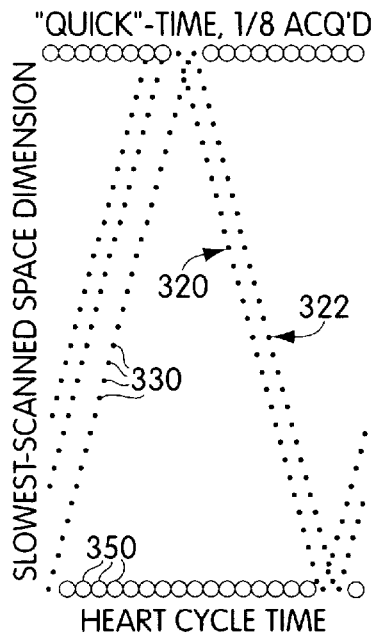
FIGS. 5A, 5B, 5C, 5D, 5E, 5F, 5G and 5H are graphs of beam position in a slow scan direction as a function of heart cycle time, illustrating acquisition of image data for a plurality of three-dimensional images at different times during a heart cycle.
Figure 5B:
Figure 5C:
Figure 5D:
Figure 5E:
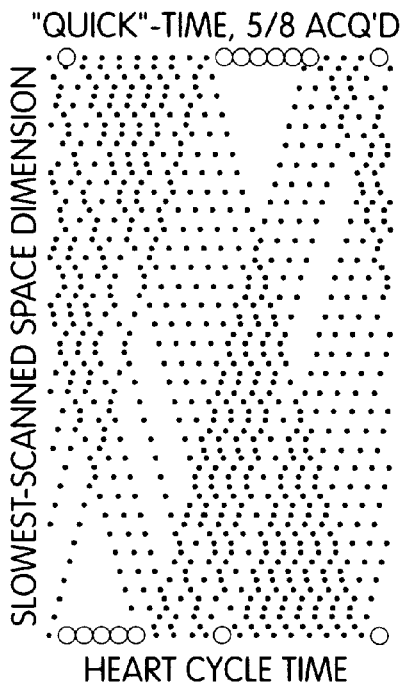
Figure 5F:
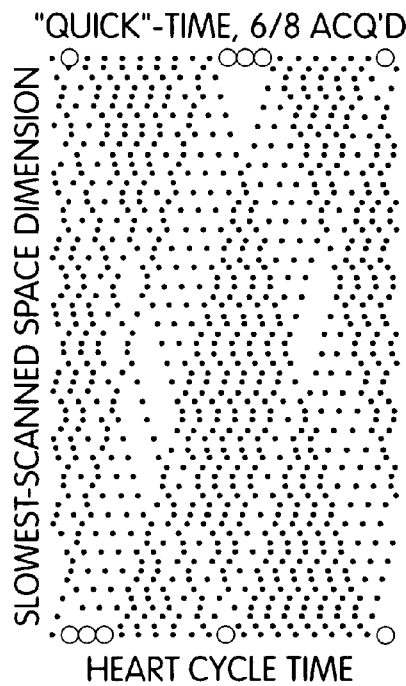
Figure 5G:
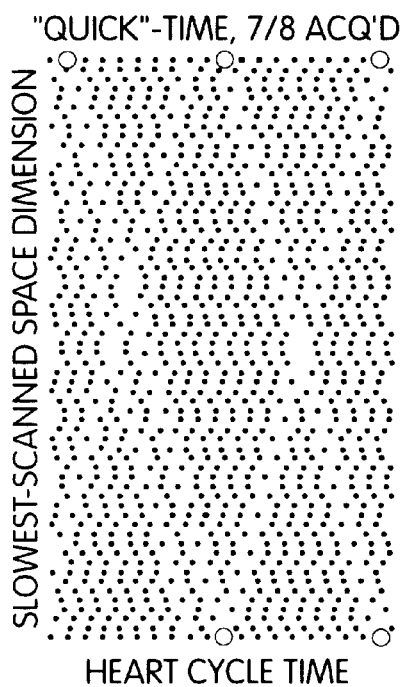
Figure 5H:
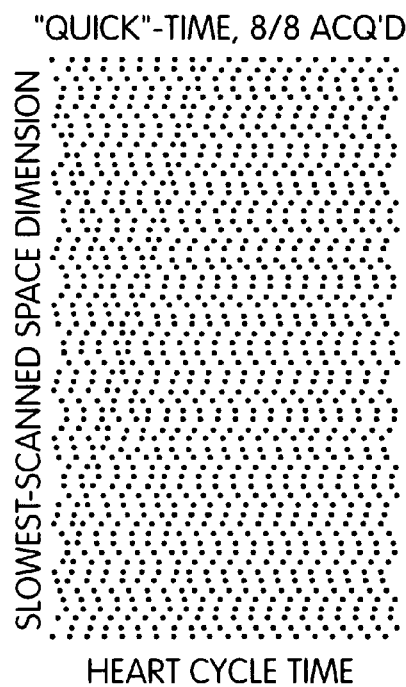

An example of a scan pattern in accordance with the invention is illustrated in FIG. 4. Ultrasound beam position in the slow scan direction is plotted in FIG. 4 as a function of time in units of cardiac cycles. Scanning in the slow scan direction is represented by scan path 200, and acquisition of two-dimensional slices of the volume of interest is represented by dots 210, 212, etc. Each of the dots 210, 212, etc. represents a scan of a two-dimensional slice in the fast scan direction. It will be understood that the two-dimensional slice may be curved or tilted in the slow scan direction if scanning in the slow scan direction is performed simultaneously with scanning in the fast scan direction. The slow scan path 200 is bidirectional, with approximately 2.5 scans in the slow scan direction per cardiac cycle. It may be observed that the slow scan path 200 is asynchronous with the cardiac cycle. However, scanning in the slow scan direction may pause one or more times, as indicated at 220 in FIG. 4, to ensure adequate spatial sampling of the volume of interest and adequate temporal sampling of the cardiac cycle, as described in detail below.

In order to illustrate the spatial distribution of data samples over the volume of interest and the temporal distribution of data samples over the cardiac cycle, multiple slow scan paths of a three-dimensional cardiac image acquisition are shown in the time/space diagrams of FIGS. 5A–5H. As in FIGS. 2A–2D and FIGS. 3A–3D, the vertical axis represents beam position in the slow scan direction, and the horizontal axis represents time, with a single cardiac cycle being illustrated. Successive figures represent increments of one-eighth of the total acquisition time. It will be understood that multiple slow scans, performed during different cardiac cycles, are superimposed on an equivalent-time cardiac cycle. The slow scans are represented in FIGS. 5A–5H by slanted slow scan paths 320, 322, etc., each of which is made up of multiple scans in the fast scan direction. Each scan in the fast scan direction is represented by a dot 330 in FIGS. 5A–5H.

A requirement of the image data acquisition technique of the present invention is to ensure that the slanted scan paths adequately cover the area of the time/space diagram with no large, empty regions in as short a time as possible. This requirement implies approximately uniform coverage.

One possible approach is to phase lock the scanning speed in the slow scan direction to a fractional vernier multiple of the patient's heart rate, so that the scan path precesses through the time/space diagram. However, such a closed-loop feedback system with a sample rate equal to the heart rate would be difficult to make both fast and stable. Furthermore, if the patient cannot hold his or her breath and acquisition is therefore intermittent, then phase lock either has to be maintained during the breath or restored every time acquisition is resumed.

Another approach to ensure adequate time/space sampling depends on the fact that, if the scan paths are very similar in shape and slope, then they uniformly cover the diagram if and only if they uniformly intersect the time axis. Thus, if the scan paths start from one or both ends of the slow scan space at a set of uniformly-spaced time intervals, then the scan paths will uniformly cover the area. The order in which the starting time points are used is irrelevant. The number of time samples in the cardiac cycle depends on the desired number of images of the volume of interest during the patient's cardiac cycle, which is the total acquisition time divided by the time to sample the volume of interest once. The number of time samples in the cardiac cycle does not depend on the length of the cardiac cycle.

The scanning speed in the slow scan direction is the translation factor between two-dimensional frame rate and the desired sample rate in the slow scan dimension. The optimum speed in the slow scan direction produces the desired spatial sample rate for the maximum two-dimensional frame rate at the required imaging depth. A slower than optimum speed in the slow scan direction increases the acquisition time, and a faster than optimum speed requires more passes through the time/space area to acquire sufficient spatial samples. Also, with mechanical scanning, a faster than optimum speed produces more wear, heating and noise than necessary. For bidirectional scanning, the optimum scanning speed is twice as high; even spatial samples are acquired in one direction, and odd spatial samples are acquired in the other direction.

The time sampling interval can be determined by specifying either the number of time samples per cardiac cycle or the total acquisition time, together with measurement of the cardiac cycle time. For any particular system speed, the choice of time sampling interval involves a tradeoff between acquisition time and quality of the reconstructed images. The system constructs a set, preferably an ordered list, of every integer multiple of the time sampling interval from zero through the cardiac cycle time. The list is called an available departure time (ADT) list. Unidirectional scanning uses a single ADT list, while bidirectional scanning may use one or two ADT lists.

When data acquisition begins and at the completion of each scan in the slow scan direction, the system compares the time since the most recent ECG trigger to unused ADT's in the ADT list. An unused ADT is selected which has a time greater than or equal to the current time from the most recent ECG trigger. Preferably, the ADT closest to the current time is selected. The system pauses spatial scanning, if necessary, until the selected ADT time is reached and then resumes scanning. As data acquisition progresses, the selected ADT's are deleted from the list or are marked as used. When the list is completely used, data acquisition is complete.

Correct reconstruction of the acquired data into images of the volume of interest requires keeping a record of the time of every ECG trigger and the time of the start of each scan in the slow scan direction, either relative to each other or relative to a time reference, such as the start of acquisition. This information may be recorded in various equivalent ways. The acquired image data may be resorted into a more easily accessible order as it is being acquired or as part of scan conversion processing.

With reference to the time/space diagrams of FIGS. 5A–5H, the ADT's can be represented as a uniformly spaced set of bubbles on the horizontal time axis, which disappear when the departure times are used. Bubbles are used on the top and bottom axes if two ADT lists are used for bidirectional scanning. To progress through the diagrams during data acquisition, the system starts at a bubble 350 and scans along a slanted scan path, aliasing back to time equals zero at the beginning of each cardiac cycle. At the end of each slanted scan path, the system slides to the right (pauses scanning) to the next unused bubble 350 and starts scanning along a new slanted scan path. The diagram is approximately uniformly covered when all the ADT bubbles disappear. Any additional scan paths would provide redundant data samples. If the scan paths have a consistent shape and slope, and their intercepts on the time axis are uniform, then the scan paths are uniform over the entire time/space area.

Scan conversion involves interpolating and resampling the acquired data onto a more convenient uniform grid. For the scanning techniques disclosed herein, scan conversion is a four-dimensional operation, and the four dimensions are not exactly orthogonal (separable). However, the fast scan dimensions can be approximated as orthogonal, and it may be possible to interpolate the slow scan dimensions separately, for example, if the transducer has position feedback so that the space dimension is uniformly sampled.

Scan conversion following data acquisition in accordance with the invention is a four-dimensional operation. Strictly, the four dimensions are not separable. Scan conversion interpolations may be either a single non-separable step (interpolating between the 16 nearest data samples according to distance), or a combination of simpler steps (interpolating separately in dimensions that are sufficiently orthogonal).

The simplifying assumption of instantaneous sampling of the two fast scan space dimensions is not precisely true. Because of the movement in the slow scan direction, the two-dimensional slices are not the planes that would obtained if the scanning in the slow scan direction was stepped, but rather slightly slanted planes or slightly curved surfaces. However, that effect is deterministic and known in advance, so the scan conversion interpolation and resampling can take the effect into account and eliminate the slight geometric distortion. The distortion does not directly affect image quality. Because the distortion of the two-dimensional slices is a large scale, but small magnitude, twist or warp, it may be ignored. For bidirectional scanning in the slow scan direction, the scanning direction in the fast scan dimensions should be reversed when the slow scan direction is reversed, so that the distortion is similar for all parts of the data.

As indicated above, the cardiac cycle time varies. For example, the heart rate tends to increase by approximately one percent per second during a breath hold. This makes the right edge of the time/space diagram at the end of the cardiac cycle uneven, an effect which has been ignored except for a binary choice of keeping or discarding data sets. Data acquired during very aberrant heartbeats should be discarded. The discarded data can be either reacquired or reconstructed with interpolation. If the remaining variations in cardiac cycle time are not compensated, then the reconstructed image quality tends to degrade.

Since the ECG trigger times are recorded in the ADT algorithm for aliasing the data into the equivalent-time cardiac cycle, it is possible to compensate for slight cardiac cycle time variations by slight time rescaling. This slightly changes the slopes of the scan paths in the time/space diagram, which is equivalent to a slight variation in acquisition speed. The data can be interpolated and resampled on the new time scale before scan conversion, but since scan conversion is inherently an interpolation and resampling operation, the time rescaling can be included in the scan conversion processing. Time rescaling complicates the computation of addresses and interpolation coefficients, but since the location of all the data is known in all four dimensions, it is a computation in analytical geometry. The main drawback is that the geometric distortion due to heart cycle variations changes from one acquisition to the next and cannot be calculated in advance, unlike the other geometric distortions.

For rotational scanning in the slow scan direction where the two-dimensional frames at the ends of the slow scan should align (180° rotation), the scan lines in the two-dimensional frames should be acquired starting in the middle and progressing outwardly (alternating right and left), or starting at the edges and progressing inwardly, rather than the usual monotonic sweep. This makes the curvature of the two-dimensional frames in the slow scan direction have a shallow "S" shape instead of a shallow "C" shape, so that the curvature matches when the frames are rotated by 180°.

Figure 6:
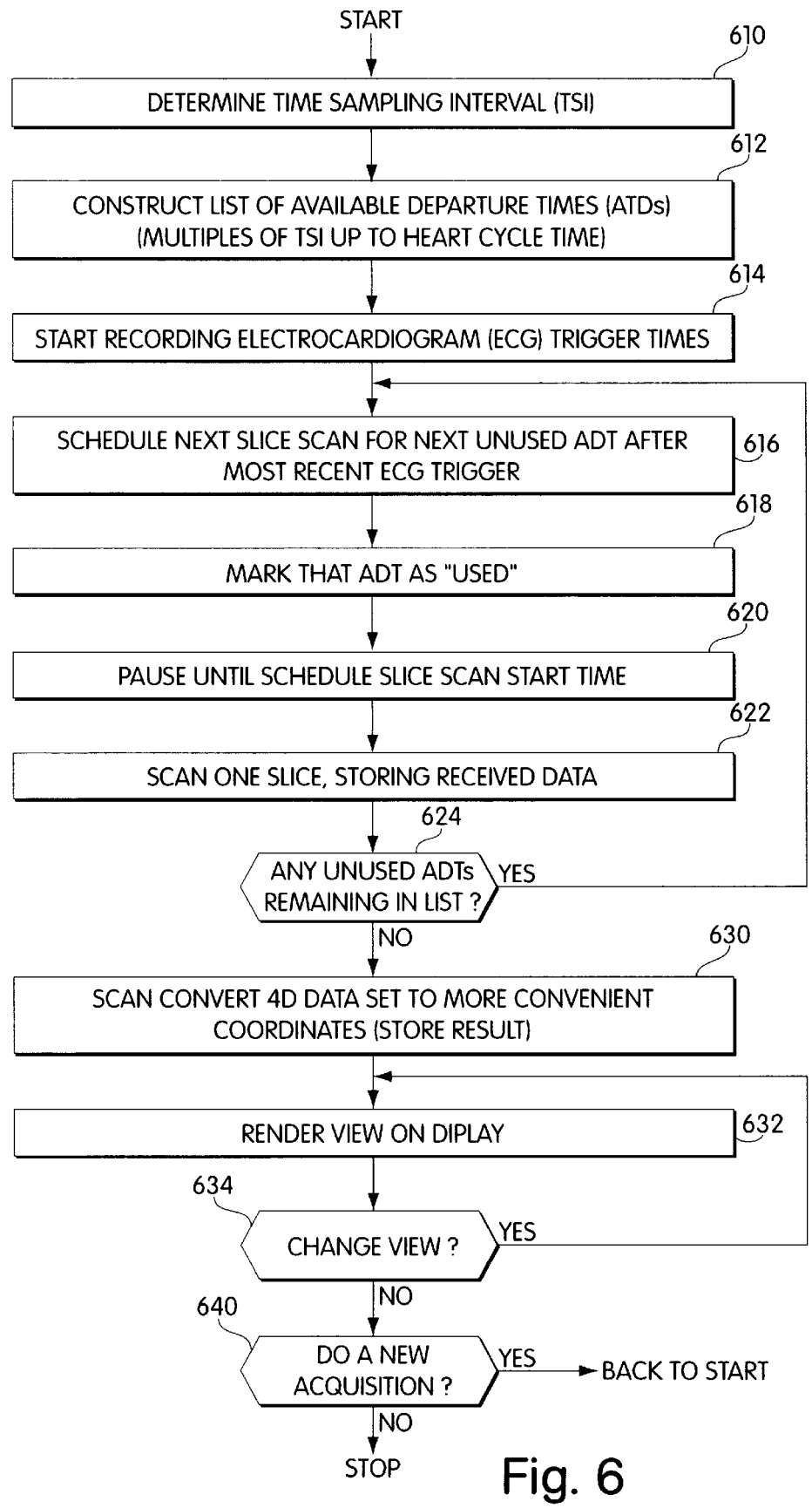
FIG. 6 is a flow chart which illustrate an embodiment of a process of image data acquisition in accordance with the invention.

A flow chart of an embodiment of a process for image data acquisition in accordance with the invention is shown in FIG. 6. In step 610, a time sampling interval (TSI) is determined. The time sampling interval establishes the number of three-dimensional images acquired during the patient's cardiac cycle. Typically, 10 to 30 images per cardiac cycle provide adequate time resolution without requiring an unacceptable acquisition time. With reference to FIGS. 5A to 5H, the time sampling interval determines the equivalent time between successive slow scans in the scan pattern.

In step 612, a list of available departure times (ADT's) is constructed. The list contains available departure times relative to a reference time in the patient's cardiac cycle, such as an ECG trigger, and an indication of whether each ADT is used or unused. The list may be stored in the memory of system controller 32 (FIG. 1).

In step 614, the system controller 32 starts recording ECG trigger times. Referring to FIG. 1, ECG trigger device 50 provides ECG trigger signals indicative of the patient's heartbeats to system controller 32. The ECG trigger times are used for synchronization of data acquisition and are later used in scan conversion.

In step 616, the next slow scan is scheduled for the first unused ADT after the most recent ECG trigger. Referring to FIGS. 5A to 5H, available departure times are represented by bubbles 350. To minimize wasted time, the first unused ADT after an ECG trigger is established as the starting time of a slow scan. In step 618, the selected ADT is marked as used in the list of available ADT's. In step 620, the system pauses, if necessary, until the scheduled scan start time. In step 622, a slow scan is performed, and the received data is stored in acoustic memory 20 (FIG. 1).

As discussed above, one slow scan involves multiple two-dimensional scans in the fast scan direction, as represented by dots 330 in FIGS. 5A to 5H. As indicated above, slow scanning may be unidirectional or bidirectional. Bidirectional scanning in the slow scan direction may be treated as a single scan or as two scans. The example of FIGS. 5A to 5H illustrates bidirectional scanning, with each direction treated as a separate slow scan. Thus, available departure times are established for starting scanning from each side of the slow scan space. The available departure times are represented by bubbles 350 at the top and bottom of each diagram in FIGS. 5A to 5H. Thus, the system establishes a first list of available departure times for upward scanning and a second list of available departure times for downward scanning. Each upward or downward slow scan is scheduled by selecting the first unused ADT after the most recent ECG trigger in step 616.

In step 624, a determination is made as to whether any unused ADT's remain in the ADT list (or ADT lists in the case of bidirectional scanning). If an unused ADT remains in the list, the process returns to step 616 for scheduling the next slow scan as described above. If all ADT's in the list have been used, the process proceeds to step 630 (FIG. 6B).

In step 630, the scan conversion and rendering unit 24 (FIG. 1) converts the acquired four-dimensional data set to a suitable form for display and stores the result in acoustic memory 20. In particular, the acquired data is interpolated to generate three-dimensional image data at selected time intervals during the patient's cardiac cycle. The three-dimensional image data may be processed as necessary to produce a desired image on video display unit 30 in step 632. In step 634, a determination is made as to whether a change of views has been requested by the user. When a changed view has been requested, the process returns to step 632 for rendering a new image of the volume of interest. If a changed view is not requested in step 634, a determination is made in step 640 as to whether a new data acquisition is required. When a new data acquisition is required, the process returns to step 610 (FIG. 6A) to begin a new data acquisition. Otherwise the process is complete.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for medical ultrasound imaging of a volume of interest in a patient having a cardiac cycle, comprising the steps of:

scanning an ultrasound beam in a fast scan direction;

scanning the ultrasound beam in a slow scan direction concurrently with scanning in the fast scan direction, by performing multiple scans across the entire volume of interest during multiple cardiac cycles;

during scanning of the ultrasound beam, acquiring ultrasound data samples, representative of two-dimensional slices of the volume of interest in the patient, at different points in the slow scan direction and at different times in the patient's cardiac cycle, by acquiring a subset of a desired set of data samples during each of the multiple scans across the entire volume of interest;

controlling scanning in the slow scan direction relative to the patient's cardiac cycle so that the acquired data samples have a desired spatial distribution over the volume of interest and a desired temporal distribution over the patient's cardiac cycle; and converting the acquired data samples to three-dimensional image data sets which represent the volume of interest at different times in the patient's cardiac cycle.

2. A method as defined in claim 1 wherein the step of controlling scanning in the slow scan direction comprises starting scanning in the slow scan direction at uniformly spaced time intervals relative to the patient's cardiac cycle.

3. A method as defined in claim 1 wherein the step of controlling scanning in the slow scan direction comprises defining a plurality of available departure times relative to the patient's cardiac cycle, selecting an unused departure time from the available departure times, starting scanning in the slow scan direction at the selected departure time and marking the selected departure time as used.

4. A method as defined in claim 1 wherein the step of controlling scanning in the slow scan direction comprises selecting the spatial and temporal distributions of the acquired data samples such that spatial and temporal variations in an object being imaged may be reconstructed.

5. A method as defined in claim 1 wherein the step of controlling scanning in the slow scan direction comprises controlling scanning such that the acquired data samples have a substantially uniform spatial distribution over the volume of interest and have a substantially uniform temporal distribution over the patient's cardiac cycle.

6. A method as defined in claim 1 wherein the step of scanning the ultrasound beam in the slow scan direction comprises unidirectional scanning in the slow scan direction.

7. A method as defined in claim 1 wherein the step of scanning the ultrasound beam in the slow scan direction comprises bidirectional scanning in the slow scan direction.

8. A method as defined in claim 1 wherein the step of scanning the ultrasound beam in the slow scan direction comprises continuous scanning in the slow scan direction.

9. A method as defined in claim 8 wherein the step of continuous scanning comprises scanning at a constant speed in a slow scan space.

10. A method as defined in claim 1 wherein the step of scanning the ultrasound beam in the slow scan direction comprises stepped scanning in the slow scan direction.

11. A method as defined in claim 1 wherein the step of scanning the ultrasound beam in the slow scan direction comprises scanning at a speed that is based on a scanning speed in the fast scan direction and a desired sample spacing in the slow scan direction.

12. A method as defined in claim 1 wherein the step of scanning the ultrasound beam in the slow scan direction comprises mechanical scanning of an ultrasound transducer.

13. A method as defined in claim 1 wherein the step of scanning the ultrasound beam in the slow scan direction comprises electronic scanning of the ultrasound beam with a phased array ultrasound transducer.

14. A method as defined in claim 1 wherein the step of scanning the ultrasound beam in the fast scan direction comprises electronic scanning of the ultrasound beam with a phased array ultrasound transducer.

15. A method as defined in claim 1 wherein the step of controlling scanning in the slow scan direction comprises phase locking scanning in the slow scan direction to a fractional vernier multiple of the patient's cardiac cycle rate.

16. A method as defined in claim 1 wherein the step of scanning the ultrasound beam in the fast scan direction comprises free running scanning in the fast scan direction.

17. A method as defined in claim 1 wherein the step of scanning the ultrasound beam in the fast scan direction comprises triggering scanning in the fast scan direction in response to a position signal representative of the position of the ultrasound beam in the slow scan direction.

18. Apparatus for medical ultrasound imaging of a volume of interest in a patient having a cardiac cycle, comprising:

an ultrasound transducer comprising an array of transducer elements;

a transmit beamformer for energizing said transducer elements for transmitting an ultrasound beam into a volume of interest in the patient's body and for scanning the ultrasound beam in a fast scan direction;

a scanning device for scanning the ultrasound beam in a slow scan direction, concurrently with scanning in the fast scan direction, by performing multiple scans across the entire volume of interest during multiple cardiac cycles;

a receive beamformer for processing received signals, generated by said transducer elements in response to ultrasound echoes received from the volume of interest, to form at least one receive beam for each of the transmitted ultrasound beams, wherein said receive beamformer acquires ultrasound data samples, representative of two-dimensional slices of the volume of interest, at different points in the slow scan direction and at different times in the patient's cardiac cycle, by acquiring a subset of a desired set of data samples during each of the multiple scans across the entire volume of interest;

an ECG device coupled to the patient for generating an ECG signal representative of the patient's cardiac cycle;

a controller responsive to said ECG signal for controlling said scanning device so that the acquired data samples have a desired spatial distribution over the volume of interest and a desired temporal distribution over the patient's cardiac cycle; and a scan converter for converting the acquired data samples to three-dimensional image data sets which represent the volume of interest at different times in the patient's cardiac cycle.

19. Apparatus for medical ultrasound imaging as defined in claim 18 wherein said controller comprises means for starting scanning in the slow scan direction at uniformly spaced time intervals relative to the patient's cardiac cycle.

20. Apparatus for medical ultrasound imaging as defined in claim 18 wherein said controller comprises means for defining a plurality of available departure times relative to the patient's cardiac cycle, means for selecting an unused departure time from the available departure times, means for starting scanning in the slow scan direction at the selected departure time and means for marking the selected departure time as used.

21. Apparatus for medical ultrasound imaging as defined in claim 18 wherein said controller comprises means for controlling said scanning device such that the acquired data samples have a substantially uniform spatial distribution over the volume of interest and have a substantially uniform temporal distribution over the patient's cardiac cycle.

22. Apparatus for medical ultrasound imaging as defined in claim 18 wherein said scanning device comprises a mechanical scanning device.

23. Apparatus for medical ultrasound imaging as defined in claim 18 wherein said scanning device comprises a motor for moving said ultrasound transducer.

24. Apparatus for medical ultrasound imaging as defined in claim 18 wherein said scanning device comprises means for electronic scanning of the ultrasound beam.

* * * * *